United States Patent
Okamoto et al.

(10) Patent No.: US 7,323,101 B2
(45) Date of Patent: Jan. 29, 2008

(54) SEPARATING AGENT FOR OPTICAL ISOMER AND METHOD FOR PREPARATION THEREOF

(75) Inventors: Yoshio Okamoto, Aichi (JP); Chiyo Yamamoto, Aichi (JP); Takateru Kubota, Aichi (JP)

(73) Assignee: Daicel Chemical Industries, Ltd., Osaka (JP)

( * ) Notice: Subject to any disclaimer, the term of this patent is extended or adjusted under 35 U.S.C. 154(b) by 73 days.

(21) Appl. No.: 10/509,506

(22) PCT Filed: Apr. 23, 2003

(86) PCT No.: PCT/JP03/05196

§ 371 (c)(1), (2), (4) Date: Sep. 28, 2004

(87) PCT Pub. No.: WO03/091185

PCT Pub. Date: Nov. 6, 2003

(65) Prior Publication Data

US 2005/0222454 A1 Oct. 6, 2005

(30) Foreign Application Priority Data

Apr. 25, 2002 (JP) ......................... PCT/JP02/04162
Apr. 26, 2002 (JP) ............................. 2002-125666

(51) Int. Cl.
*B01D 15/08* (2006.01)
(52) U.S. Cl. ............................... 210/198.2; 210/502.1; 210/635; 210/656; 502/404
(58) Field of Classification Search .............. 210/635, 210/656, 659, 198.2, 502.1; 502/401, 402, 502/404
See application file for complete search history.

(56) References Cited

U.S. PATENT DOCUMENTS 5,302,633 A   4/1994   Kimata et al.
6,117,325 A * 9/2000   Oda et al. .................. 210/635
6,217,769 B1 * 4/2001   Okamoto et al. ........... 210/635

FOREIGN PATENT DOCUMENTS

| EP | 0 656 333 A1 | 6/1995 |
| EP | 0 978 498 A1 | 2/2000 |
| JP | 4-202141 | 7/1992 |
| JP | 7-30122 | 4/1995 |
| JP | 11-171800 | 6/1999 |

OTHER PUBLICATIONS

Kimata, PTO Translation No. 06-3034 of Japan Patent No. 4-202141, Mar. 2006.*
Hirata, PTO Translation No. 06-3081 of Japan Patent No. 4-158260, Mar. 2006.*
esp@cenet Abstract of Japan Patent No. 62-270602.*
"Useful Chiral Packing Materials for High-Performance Liquid Chromatographic Resolution of Enantiomers: Phenylcarbamates of Polysaccharides Coated on Silica Gel", by Yoshio Okamoto et al, J. Am. Chem. Soc., vol. 106, No. 18, 1984, pp. 5357-5359.
European Patent Office Search Report dated Sep. 27, 2005.

* cited by examiner

*Primary Examiner*—Ernest G. Therkorn
(74) *Attorney, Agent, or Firm*—Flynn, Thiel, Boutell & Tanis, P.C.

(57) ABSTRACT

A separating agent which combines a high optical resolving power inherent in polysaccharide derivatives with sufficient solvent resistance and a method with which the separating agent can be produced efficiently in short steps. The separating agent for enantiomeric isomers is characterized in that a polymerizable polysaccharide derivative of a polysaccharide derivative having polymerizable functional groups and a polymerizable monomer having polymerizable unsaturated groups are copolymerized with a carrier having polymerizable functional groups to be chemically bound mutually. The separating agent is preferably used for high performance liquid chromatography (HPLC) and has an excellent solvent resistance.

10 Claims, 1 Drawing Sheet

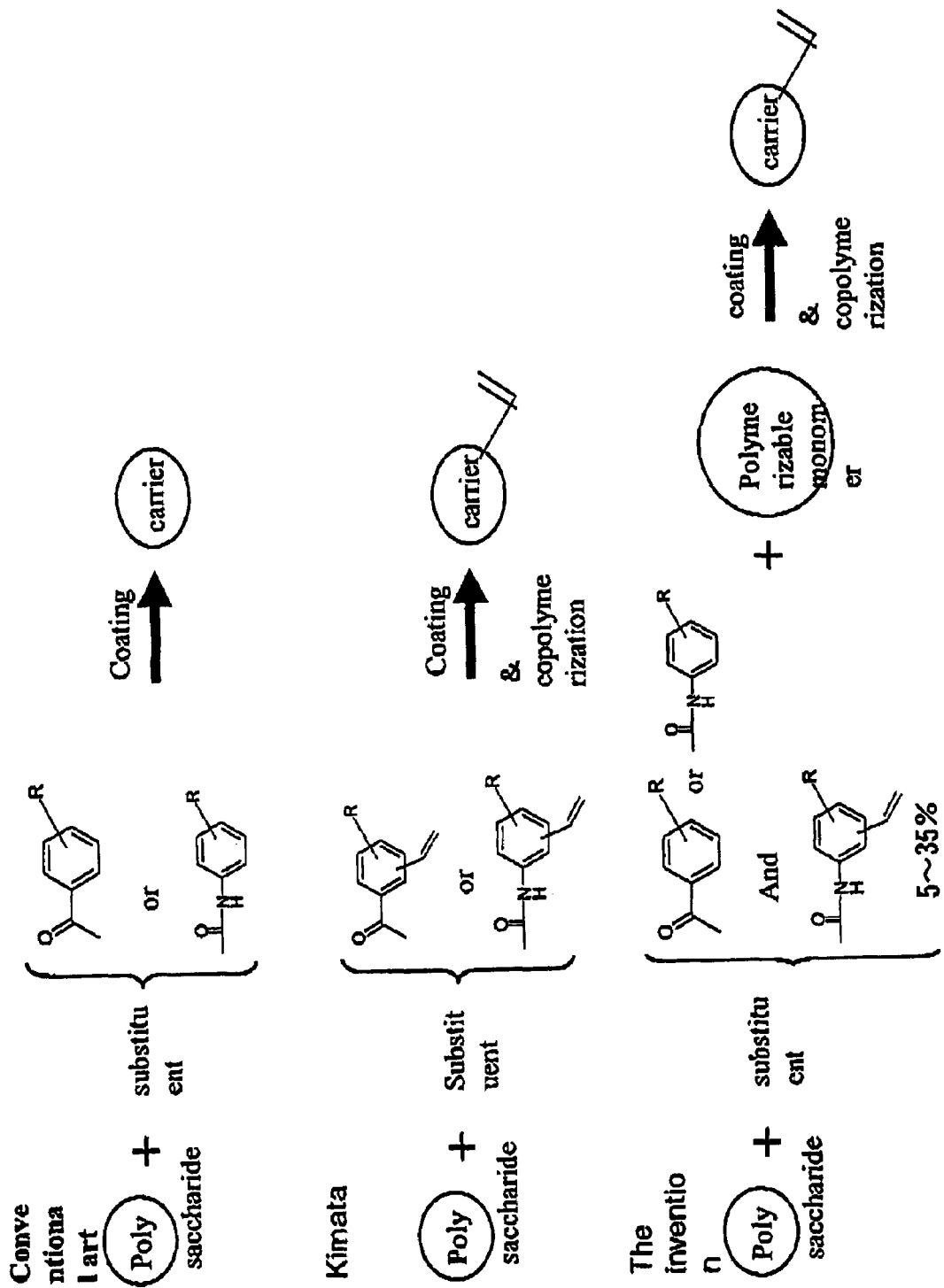

SEPARATING AGENT FOR OPTICAL ISOMER AND METHOD FOR PREPARATION THEREOF

REFERENCE TO RELATED APPLICATIONS

This application is a 371 of PCT/JP03/05196 filed Apr. 23, 2003.

TECHNICAL FIELD TO WHICH THE INVENTION BELONGS

The present invention relates to a separating agent for enantiomeric isomers, a method of producing the same, and a method of separating enantiomeric isomers. In particular, the present invention relates to a separating agent which is suitably used for high performance liquid chromatography (HPLC) and has an excellent solvent resistance and a method of producing the same, as well as a method of separating enantiomeric isomers with the use of the same.

PRIOR ART

It has been previously well known that polysaccharides and derivatives thereof such as ester and carbamate derivatives of cellulose and amylose exhibit a high optical resolving power. It has been also well known that chromatographic separating agents where those substances are physically adsorbed and supported on silica gel are excellent separating agents exhibiting an optical resolving power over a wide range, a good theoretical plate number, and good durability (Y. Okamoto, M. Kawashima and K. Hatada, J. Am. Chem. Soc., 106, 5357, 1984).

However, those separating agents can be employed only under restricted separation conditions, since polysaccharide derivatives are supported on silica gel via physical adsorption and thus solvents in which the polysaccharide derivatives are soluble can not be used as the mobile phase, etc. Also, solvents in which samples are to be dissolved are restricted. In the case of a sample having a low solubility in a solvent usable as the mobile phase, there arises a serious problem, particularly for chromatographic separation. Moreover, there is another inconvenience that only limited washing fluids are usable in washing away contaminants strongly adsorbed on the separating agents. In view of those points, a separating agent carrying a polysaccharide derivative thereon and having a high solvent resistance has been required.

To solve those problems, a method where a polysaccharide derivative is immobilized on a carrier has been proposed. For example, JP 4-202141 A discloses a separating agent for enantiomeric isomers where a polysaccharide derivative in which a vinyl group is introduced into a hydroxy position of the polysaccharide via an ester bond or a urethane bond is directly copolymerized with a porous carrier where a vinyl group is introduced.

Also, the inventors of the present invention have previously demonstrated a technology that a polysaccharide derivative is chemically bound to a silica gel via an isocyanate derivative to assure stability in JP 7-30122 B, and further proposed a method of immobilizing including performing radical copolymerization and meshing of styrene and divinylbenzene on silica gel on which a cellulose derivative is supported in JP 11-171800 A.

However, those methods have not been suited for industrial production owing to problems in that it is necessary to prepare a special isocyanate derivative, there are many production steps, and the production steps become complex. Moreover, when the immobilization rate of a polysaccharide derivative is increased, a high optical resolving power inherent in the polysaccharide derivative is lost. On the other hand, to retain the high optical resolving power, it is necessary to reduce the immobilization rate of the polysaccharide derivative. Thus, there has been no separating agent for enantiomeric isomers, which combines the high optical resolving power inherent in the polysaccharide derivative with sufficient solvent resistance.

Therefore, there has been strongly desired a separating agent for enantiomeric isomers which combines the high optical resolving power inherent in the polysaccharide derivatives with solvent resistance, and further can be produced in short steps.

DISCLOSURE OF THE INVENTION

The present invention has been conducted in view of the above-mentioned circumstances, and a purpose of the present invention is to provide a separating agent which combines a high optical resolving power inherent in polysaccharide derivatives with sufficient solvent resistance and a method with which the separating agent can be produced efficiently in short steps.

The inventors of the present invention have completed the present invention as a result of intensive study on a separating agent for enantiomeric isomers, which combines the high optical resolving power inherent in the polysaccharide derivatives with sufficient solvent resistance, to solve the above problem.

The present invention relates to a separating agent for enantiomeric isomers, comprising a polymerizable polysaccharide derivative of a polysaccharide derivative having polymerizable functional groups and a polymerizable monomer having polymerizable unsaturated groups, the polymerizable polysaccharide derivative and the polymerizable monomer having been copolymerized with a carrier having polymerizable functional groups to be chemically bound mutually.

Further, the present invention relates to a method of producing a separating agent for enantiomeric isomers, comprising the step of copolymerizing a polymerizable polysaccharide derivative of a polysaccharide derivative having polymerizable functional groups and a polymerizable monomer having polymerizable unsaturated groups with a carrier having polymerizable functional groups to be chemically bound mutually.

It is preferable that the polymerizable polysaccharide derivative be supported on the carrier having polymerizable functional groups followed by being copolymerized with the polymerizable monomer. Derivatization of the polysaccharide and introduction of the polymerizable functional groups may be simultaneously performed when the polymerizable polysaccharide derivative is synthesized.

Furthermore, the present invention provides a method of separating enantiomeric isomers using the above separating agent for enantiomeric isomers or using the separating agent for enantiomeric isomers obtained by the above production method. Additionally, the present invention provides for the use of those compounds for enantiomeric isomer separation.

It is preferred that the polysaccharide derivative have a polymerizable functional group at position 6. However, the polysaccharide derivative may have the polymerizable functional group at a position other than position 6.

DETAILED DESCRIPTION OF THE INVENTION

Modes for carrying out the present invention are described in detail below.

The polysaccharide to be used in the present invention may be any polysaccharide, regardless of whether it is a synthetic polysaccharide, a natural polysaccharide or modified natural polysaccharide, so far as it is optically active. Preferably, it has a high regularity in its binding form. Examples of the polysaccharide include a β-1,4-glucan (cellulose), α-1,4-glucan (amylose, amylopectin), α-1,6-glucan (dextran), β-1,6-glucan (pustulan), β-1,3-glucan (for example, curdlan, schizophyllan, etc.), α-1,3-glucan, β-1,2-glucan (Crown Gall polysaccharide), β-1,4-galactan, β-1,4-mannan, α-1,6-mannan, β-1,2-fructan (inulin), β-2,6-fructan (levan), β-1,4-xylan, β-1,3-xylan, β-1,4-chitosan, α-1,4-N-acetylchitosan (chitin), pullulan, agarose, alginic acid, etc. as well as amylose-containing starch. Among these, cellulose, amylose, β-1,4-xylan, β-1,4-chitosan, chitin, β-1,4-mannan, inulin, curdlan, etc., from which high purity polysaccharides are readily available, are preferred, with cellulose and amylose being particularly preferred.

The number average degree of polymerization (average number of pyranose or furanose rings contained in one molecule) of these polysaccharides is preferably 5 or more, more preferably 10 or more. There is no particular upper limit in the number average degree of polymerization but it is desirably 1,000 or less in consideration of ease of handling.

Polysaccharide derivatives used for the present invention include compounds obtained by derivatizing by binding compounds having functional groups capable of reacting with a hydroxy group to a part of the hydroxy groups of the polysaccharide as the above via ester bonds or urethane bonds using methods conventionally and publicly known. Here, the compounds having functional groups capable of reacting with a hydroxy group may be any of isocyanate derivatives, carboxylic acids, esters, acid halides, acid amides, halides, epoxy compounds, aldehydes, alcohols, and compounds having other leaving groups, and it is possible to use aliphatic, alicyclic, aromatic, and heteroaromatic compounds thereof. Of those compounds, particularly, phenylisocyanate compounds substituted with halogen atoms or alkyl groups having 1 to 3 carbons are suitably used. Particularly preferable ones as the polysaccharide derivatives used for the present invention are ester or carbamate derivatives of polysaccharides having 0.1 or more ester or urethane bonds per monosaccharide.

Moreover, the polymerizable polysaccharide derivative used for the present invention is produced by performing chemical modification of the polysaccharide using the same compound as above having a polymerizable unsaturated group typified by, for example vinyl bonds, upon the formation of the foregoing polysaccharide derivative. Compounds having polymerizable unsaturated groups publicly known which react with the hydroxy groups of the polysaccharide to produce ester bonds or urethane bonds are appropriately selected, and examples thereof include: unsaturated acid halides such as acryloyl chloride, methacryloyl chloride, and vinylbenzoyl chloride; and unsaturated isocyanates such as vinylphenylisocyanate and isocyanate ethyl methacrylate. Also, furthermore, a single or multiple polymerizable unsaturated groups may be present.

The percentage of polymerizable unsaturated groups present in the polymerizable polysaccharide derivative is from 5 to 50%, and preferably from 5 to 35%, based on the hydroxy groups of the polysaccharide.

The polymerizable polysaccharide derivative in the present invention is configured by: converting a part of the hydroxy groups of the aforementioned polysaccharide into ester groups or carbamate groups; and further substituting a part of the substituents by the predetermined polymerizable unsaturated groups.

It is preferred that the polymerizable unsaturated groups be selectively introduced into a part of the hydroxy groups at position 6 of the polysaccharide.

Alternatively, there is also a method where the introduced position of the polymerizable unsaturated groups are not limited by simultaneously performing a step of substituting a part of the hydroxy groups of a part of the polysaccharide by ester groups or carbamate groups and a step of introducing the polymerizable unsaturated groups via the ester groups or the carbamate groups. Employing such a synthesis method can make the synthesis step of the polymerizable polysaccharide derivative one stage and simplify the synthesis to a large extent.

The carrier to be used in the present invention includes a porous organic carrier or porous inorganic carrier, with the porous inorganic carrier being preferred. Suitable examples of the porous organic carrier include high polymers such as polystyrene, polyacrylamide, and polyacrylate. Suitable examples of the porous inorganic carrier include silica, alumina, magnesia, glass, kaolin, titanium oxide, silicates, hydroxyapatite, etc. A particularly preferred carrier is silica gel, the particle size of which is preferably 1 to 300 μm, more preferably 1 to 100 μm. The average pore size thereof is preferably 200 to 8,000 Angstroms, more preferably 200 to 4,000 Angstroms. To exclude the possible influence of the remaining silanol on the surface, it is desirable that surface treatment is performed. However, there is no problem if no surface treatment is performed at all.

Used in the present invention is a carrier having a polymerizable unsaturated group, synthesized by a method publicly known using the same compound as above having a polymerizable unsaturated group typified by, for example, a vinyl bond. JP-A 4-202141 discloses a specific method of introducing the polymerizable unsaturated group into the carrier. Included in the present invention is a method of introducing an acryl group or a methacryl group as the polymerizable unsaturated group including: performing aminoalkylation of a silica gel's surface using 3-aminopropylsilane for the hydroxy group (silanol group) on the silica gel surface; and reacting (meth)acryloyloxyalkyl isocyanate with the amino group, or a method of introducing an objective polymerizable unsaturated group including directly reacting a silane treating agent containing an unsaturated group typified by 3-(trimethoxysilyl)propyl methacrylate with silica gel.

In the present invention, the polymerizable unsaturated group introduced into the polysaccharide derivative and the polymerizable unsaturated group introduced into the carrier may be the same or different.

The present invention is intended to enhance an immobilization rate of a polymerizable polysaccharide derivative and thus improve its solvent resistance by: further using a polymerizable unsaturated monomer along with the polymerizable polysaccharide derivative and the carrier having the polymerizable unsaturated group; and performing radical copolymerization of these three polymerizable unsaturated groups. It is possible to use as the polymerizable unsaturated monomer various low molecular monomers publicly known having an ethylenic double bond. Examples thereof include: hydrocarbon compounds having a vinyl group such as styrene, divinylbenzene, butadiene, dimethylbutadiene, and isoprene; methacrylate derivatives such as methacrylate and methacrylate amide; acrylate derivatives such as acrylate and acrylate amide; and compounds containing silicon. Each of those is used alone or multiple types are used in combination. Of those, particularly, styrene and divinylbenzene are suitably used. Furthermore, the polymerizable unsaturated group introduced into the polysaccharide derivative and the polymerizable unsaturated group introduced into the carrier, and further the polymerizable unsaturated monomer may be of the same type or different types, but it is preferred that the polymerizable unsaturated monomer be different from the polymerizable unsaturated group introduced into the polysaccharide derivative and the polymerizable unsaturated group introduced into the carrier.

The polymerizable unsaturated monomer is added at an appropriate ratio to the extent that the monomer does not adversely affect the effective optical resolving power of the polymerizable polysaccharide derivative which is subject to the copolymerization. Generally, the monomer is added at a ratio of 1 to 50 parts by weight, preferably 5 to 30 parts by weight, and more preferably 5 to 15 parts by weight based on 100 parts by weight of the polymerizable polysaccharide derivative.

According to the present invention, when radical copolymerization of the polymerizable polysaccharide derivative with the carrier having the polymerizable unsaturated group and the polymerizable unsaturated monomer is performed, it is preferable to precedently support the polymerizable polysaccharide derivative on the carrier having the polymerizable unsaturated group. The amount of the polysaccharide derivative supported on the carrier is preferably from 10 to 60% by weight and, desirably, from 15 to 45% by weight based on the carrier. The polymerizable polysaccharide derivative is supported on the carrier having the polymerizable unsaturated group, and subsequently the polymerizable unsaturated monomer and a radical initiator are added with an appropriate solvent to copolymerize the objective polymerizable polysaccharide derivative, the carrier having the polymerizable unsaturated group, and the polymerizable unsaturated monomer. Those publicly known such as α,α'-azobisisobutyronitrile (AIBN) are appropriately used as the radical initiator used in this reaction.

The immobilization rate of the polysaccharide derivative in the present invention is calculated as follows. The separating agent for enantiomeric isomers obtained by performing the radical copolymerization of the polymerizable polysaccharide derivative with the carrier having the polymerizable unsaturated group and the polymerizable unsaturated monomer in the above described method is washed with a solvent which is different depending on the type of the polysaccharide derivative, for example, a solvent such as tetrahydrofuran (THF), acetone, or chloroform which solubilizes the polysaccharide derivative. Subsequently, the polymerizable polysaccharide derivative or the polysaccharide derivative eluted in the washing solution is collected. The obtained polymerizable polysaccharide derivative or polysaccharide derivative is dissolved in a heavy solvent and methanol at a known amount is added to the solution, followed by measuring by NMR. Then, the weight of the precipitated polymerizable polysaccharide derivative or polysaccharide derivative is calculated from the peak intensity ratio of methanol to the polymerizable polysaccharide derivative or the polysaccharide derivative. The immobilization rate is calculated in conjunction with the weight of the polymerizable polysaccharide derivative or polysaccharide derivative adsorbed on the carrier before the polymerization. The immobilization rate of the present invention is preferably 70% or more, and more preferably 80% or more. A washing method for the separating agent for enantiomeric isomers in this method includes a method in which washing is performed 1 to 3 times using about 5 to 40 ml of a polysaccharide derivative soluble solvent for 1 to 5 g of the separating agent for enantiomeric isomers.

A mean value of separation performance a values for enantiomeric isomers can be determined as follows. A separating agent is used as a filler, and filled in a stainless column with a length of 25 cm and inner diameter of 2 mm by a slurry filling method to make a column for enantiomeric isomers. Optical resolution of enantiomeric compounds is performed by liquid chromatography. Analytical conditions are the mobile phase: hexane (H)/chloroform (C)/2-propanol (I)=90/10/1, a flow rate: 0.1 or 0.2 ml/min, temperature: 25° C., and detection at 254 nm. A separation coefficient (a) was determined by the following formula.

Separation coefficient($\alpha$)=$k2'/k1'$

In the formula, $k1'=((t_1-t_0)/t_0)$ and $k2'=((t_2-t_0)/t_0)$. Those $t_1$ and $t_2$ denote elution times of respective enantiomeric isomers, and to denotes an elution time of tri-tert-butylbenzene.

The separating agent for enantiomeric isomers of the present invention is useful as a separating agent for chromatography such as gas chromatography, liquid chromatography, or thin layer chromatography, and it is preferable to use the separating agent particularly as a separating agent for liquid chromatography, and more preferably as a filler for simulated moving bed chromatography.

The separating agent for enantiomeric isomers of the present invention combines the high optical resolving power inherent in the polysaccharide derivative with sufficient solvent resistance, can be produced efficiently in short steps, and therefore is useful for the separation of various enantiomeric isomers.

EXAMPLES

The present invention is described in detail below by way of examples, but the present invention is not limited to these examples.

(A) Introduction of Polymerizable Unsaturated Groups on Silica Gel Surface

A-1: Synthesis of Unsaturated Silica Gel on which 2-methacryloyloxyethyl Group is Introduced (MA-Si)

A-1-1 Surface Treatment of Silica Gel

Aminopropylated silica gel (A-Si) was yielded by reacting 20 ml of 3-aminopropyltriethoxysilane with the hydroxy groups on the surface of silica gel as is conventionally done using 50 g of silica gel (pore diameter: 1,000 angstroms, particle size: 7 μm) to perform aminopropylation of the surface.

A-1-2 Introduction of Polymerizable Functional Groups

An amino group in an aminopropyl group on the silica gel surface was reacted with an isocyanate group of 2-methacryloyloxyethyl isocyanate by: using 3.5 g of the aminopropylated silica gel obtained in A-1-1; using 10 ml of dry toluene as a reaction medium; adding 0.187 g of 2-methacryloyloxyethyl isocyanate to the medium; and heating the mixture with reflux at 90 to 100° C. for 5 hours, to thereby yield 3.50 g of unsaturated silica gel (MA-Si) at which a 2-methacryloyloxyethyl group was introduced as a polymerizable unsaturated group.

A-2 Synthesis of Unsaturated Silica Gel on which a Propylmethacrylate Group is Introduced (M-Si)

Unsaturated silica gel (10 g) where a propylmethacrylate group was introduced on the silica gel surface (M-Si) was yielded by: using 10 g of silica gel (pore diameter: 1,000 angstroms, particle size: 7 μm); using a mixed solvent of 2,2-diphenyl-1-picrylhydrazyl (DPPH) and N,N-dimethylformamide (DMF) as a reaction medium; adding 4.3 ml of 3-(trimethoxysilyl)propyl methacrylate to the medium; and heating the mixture with reflux at 120° C. for 6 hours.

(B) Synthesis of Polymerizable Polysaccharide Derivative

B-1 Synthesis of Cellulose Phenylcarbamate Derivative Having Vinyl Groups at a Part of Position 6 (6-CVDMPC)

B-1-1 Synthesis of Cellulose 2,3-o-bis(3,5-dimethylphenylcarbamate)

Cellulose was swelled by: drying 6.02 g of cellulose (microcrystalline, Avicel, supplied from Merck) and 4.06 g of lithium chloride; subsequently adding 60 ml of dehydrated N,N-dimethylacetamide; and heating the mixture with reflux at 80° C. for 12 hours. Then, position 6 of the cellulose was protected by adding 20.6 g of triphenylmethyl chloride and 120 ml of dry pyridine and by heating again at 80° C. for 12 hours with stirring. Subsequently, hydroxy groups at position 2 and 3 of the cellulose were carbamated by adding 21.9 g of 3,5-dimethylphenyl isocyanate and by heating with stirring as it is for 12 hours.

After that, 17.5 g of the objective cellulose 2,3-o-bis(3,5-dimethylphenylcarbamate) were yielded by: collecting the obtained cellulose carbamate compound; washing the compound with methanol; and subsequently stirring the compound in 800 ml of 1% HCl-methanol to perform deprotection and reproduce the hydroxy groups at position 6.

B-1-2 Synthesis of Cellulose Phenylcarbamate Derivative Having Vinyl Groups at a Part of Position 6 (6-CVDMPC)

Cellulose 2,3-o-bis(3,5-dimethylphenylcarbamate) was dissolved by adding 90 ml of dry pyridine to 4.46 g of cellulose 2,3-o-bis(3,5-dimethylphenylcarbamate) obtained in the above B-1-1 and by heating the mixture at 90° C. with stirring. Subsequently, 2.97 g of cellulose 2,3-o-bis(3,5-dimethylphenylcarbamate)-6-o-(3,5-dimethylphenylcarbamate)/(4-vinylphenylcarbamate) (6-CVDMPC) where the hydroxy groups at position 6 were substituted by 4-vinylphenylcarbamate groups were yielded by: adding 0.85 g of 4-vinylphenyl isocyanate; subsequently adding 2.01 g of 3,5-dimethylphenyl isocyanate; and heating the mixture with stirring for 12 hours. Analyzing this product by $^1$H-NMR showed that the percentage of vinyl groups introduced at position 6 was 27.6%.

B-2 Synthesis of Cellulose Phenylcarbamate Derivative Having Methacryl Groups at a Part of Position 6 (6-CMDMPC)

14 ml of dry pyridine were added to 2.0 g of cellulose 2,3-o-bis(3,5-dimethylphenylcarbamate) obtained in the above B-1-1 and the whole was heated with stirring at 90° C. to dissolve the derivative. Then, 0.31 g of 2-methacryloyloxyethyl isocyanate was added to the mixture, and the whole was heated with stirring to confirm that the added isocyanate was completely reacted and consumed. Subsequently, 1.90 g of the objective cellulose 2,3-o-bis(3,5-dimethyl-phenylcarbamate)-6-o-(2-methacryloyloxyethyl-carbamate)/(3,5-dimethylphenylcarbamate) (6-CMDMPC) were yielded by adding 0.71 g of 3,5-dimethylphenyl isocyanate and by heating the mixture with stirring for 12 hours to perform carbamation of the remaining hydroxy groups at position 6. Also, $^1$H-NMR showed that the percentage of vinyl groups introduced at position 6 was 27%.

6-CMDMPC, where the percentage of vinyl groups introduced at position 6 was 10%, was yielded as with the above except for changing the amount of 2-methacryloyloxyethyl isocyanate.

Example 1

Synthesis of a Separating Agent where (6-CMDMPC) is Immobilized on MA-Si with Styrene 6-CMDMPC, which was the cellulose derivative obtained in the above B-2 and where the percentage of vinyl groups introduced at position 6 was 10%, was dissolved in THF, and supported at 25% by weight based on MA-Si obtained in the above A-1. Subsequently, oxygen was removed from the solution by vacuum treatment. Then, under a nitrogen atmosphere, dry α,α'-azobisisobutyronitrile (AIBN) at a mol number corresponding to 1/30 based on polymer-type vinyl groups was dissolved in 5.7 ml of anhydrous hexane, and styrene at 10% by weight based on the polysaccharide derivative was added as a third component to the solution. Then, 1.9 ml of the above prepared solution were added to 1.0 g of dried silica gel, and radical polymerization was performed in a thermostat chamber at 60° C. for 20 hours. After the polymerization has stopped, the resulting silica gel was washed twice using 20 ml of THF to yield the objective separating agent.

Meanwhile, the THF solution which had contributed to washing was collected, and subsequently THF was removed under a reduced pressure to collect the precipitated polysaccharide derivative. The collected polysaccharide derivative was dissolved in a heavy solvent, and 1 μl of methanol was added to the solution to determine the NMR. The weight of the precipitated derivative was calculated from a peak intensity ratio of methanol and the polysaccharide derivative consequently obtained, and the immobilization rate was calculated in conjunction with the weight of the derivative adsorbed to silica gel before the polymerization.

Example 2

Synthesis of Separating Agent where 6-CMDMPC (Where the Percentage of Vinyl Groups Introduced at Position 6 is 10%) is Immobilized on M-Si with Styrene The objective separating agent was yielded by the same method as that in Example 1, except that the unsaturated silica gel (MA-Si) on which 2-methacryloyloxyethyl groups were introduced was changed to the unsaturated silica gel (M-Si) obtained in the above A-2, on which propylmethacrylate groups were introduced. Moreover, the immobilization rate of the polysaccharide derivative was calculated by the same method as that in Example 1.

Example 3

Synthesis of Separating Agent where (6-CMDMPC) is Immobilized on MA-Si with Dimethylbutadiene The objective separating agent was yielded by the same method as that in Example 1, except that the third component, styrene was changed to dimethylbutadiene. Moreover, the immobilization rate of the polysaccharide derivative was calculated by the same method as that in Example 1.

Example 4

Synthesis of Separating Agent where (6-CMDMPC) is Immobilized on MA-Si with Dimethylbutadiene The objective separating agent was yielded by the same method as that in Example 1, except that the third component, styrene was changed to dimethylbutadiene at 20% by weight based on the polysaccharide derivative. Moreover, the immobilization rate of the polysaccharide derivative was calculated by the same method as that in Example 1.

Example 5

Evaluation of Optical Resolving Power

The separating agents prepared in Examples 1 and 2 were used as fillers, and filled in stainless columns each having a length of 25 cm and an inner diameter of 2 mm by a slurry filling method to make columns for enantiomeric isomers.

Using those columns, optical resolution of enantiomeric compounds shown in Table 3 was performed by liquid chromatography. Analytical conditions were the mobile phase: hexane (H)/chloroform (C)/2-propanol (I)=90/10/1, a flow rate: 0.1 or 0.2 ml/min, temperature: 25° C., and detection at 254 nm. The separation coefficient ($\alpha$) in the table was determined by the following formula.

Separation coefficient($\alpha$)=$k2'/k1'$:

In the formula, $k1'=((t_1-t_0)/t_0)$ and $k2'=((t_2-t_0)/t_0)$. Those $t_1$ and $t_2$ denote elution times of respective enantiomeric isomers, and to denotes an elution time of tri-tert-butylbenzene.

Table 1 shows the results when the mobile phase was hexane (H)/chloroform (C)/2-propanol (I)=90/10/1.

Example 6

The optical resolution of the enantiomeric compounds shown in Table 3 was performed by the same method as that in Example 5, except that the separating agents prepared in Examples 1 to 4 were used as fillers, the mobile phase was changed to hexane (H)/2-propanol=90/10, and the flow rate was changed to 0.1 ml/min. Table 2 shows the results.

Comparative Example 1

Synthesis of Separating Agent 6-CMDMPC where the Percentage of Vinyl Groups Introduced at Position 6 is 27% and is Immobilized on Silica Gel (A-Si) not having a Polymerizable Unsaturated Group with Styrene The objective separating agent was yielded by the same method as that in Example 1, except that the aminopropylated silica gel (A-Si) obtained in the above A-1-1 was used in place of the unsaturated silica gel on which 2-methacryloyloxyethyl groups were introduced (MA-Si) and an addition amount of AIBN was 1/50 based on the polysaccharide derivative. Moreover, the immobilization rate of the polysaccharide derivative was calculated by the same method as that in Example 1.

Comparative Example 2

Synthesis of Separating Agent 6-CVDMPC where the Percentage of Vinyl Groups Introduced at Position 6 is 27% and is Immobilized on MA-Si without the Addition of Styrene The cellulose derivative (6-CVDMPC) obtained in the above B-1 was dissolved in THF, and supported at a percentage of 25% by weight on MA-Si. Subsequently, oxygen was removed from the solution by vacuum treatment. Then, under a nitrogen atmosphere, dry $\alpha,\alpha'$-azobisisobutyronitrile (AIBN) at a mol number corresponding to 1/50 based on polymer type vinyl groups was dissolved in 5.7 ml of anhydrous hexane. Then, 1.9 ml of the aforementioned prepared solution were added to 1.0 g of dried silica gel, and radical polymerization was performed in a thermostat chamber at 60° C. for 20 hours. After the polymerization had been stopped, the resulting silica gel was washed twice using 20 ml of THF, and the silica gel after washing was dried to yield the objective separating agent.

Comparative Example 3

Synthesis of Separating Agent 6-CVDMPC where the Percentage of Vinyl Groups Introduced at Position 6 is 27% and is Immobilized on A-Si without the Addition of Styrene The objective separating agent was obtained by the same method as that in Comparative Example 2, except that MA-Si was changed to A-Si.

Comparative Example 4

The optical resolution of various enantiomeric compounds was performed using the separating agents prepared in Comparative Examples 1 to 3 by the same method as that in Example 3. Table 1 shows the results.

TABLE 1

| | | | H/C/I = 90/10/1 | | |
|---|---|---|---|---|---|
| Filler | Ex. 1 | Ex. 2 | Com. Ex. 1 | Com. Ex. 2 | Com. Ex. 3 |
| Silica gel | MA-Si | M-Si | A-Si | MA-Si | A-Si |
| Polysaccharide derivative | 6-CMDMPC | 6-CMDMPC | 6-CMDMPC | 6-CVDMPC | 6-CVDMPC |
| Addition amount of styrene (%) | 10 | 10 | 10 | — | — |
| Immobilization rate (%) | 90 | 80 | 99 | 70 | 50 |
| Enantiomeric compound 1 | 1.86 | 1.58 | 1.68 | 1.63 | 1.44 |
| Enantiomeric compound 2 | 1.60 | 1.95 | 1.0 | 1.4 | 1.62 |
| Enantiomeric compound 3 | 1.23 | 1.36 | 1.2 | 1.25 | 1.28 |

TABLE 1-continued

H/C/I = 90/10/1

| Filler | Ex. 1 | Ex. 2 | Com. Ex. 1 | Com. Ex. 2 | Com. Ex. 3 |
|---|---|---|---|---|---|
| Enantiomeric compound 4 | 1.21 | 1.23 | 1.2 | 1.15 | 1.16 |
| Enantiomeric compound 5 | 1.37 | 1.31 | 1.36 | 1.3 | 1.28 |
| Enantiomeric compound 6 | 2.52 | 3.15 | 2.5 | 2.41 | 2.45 |
| Enantiomeric compound 7 | 1.0 | 1.0 | 1.0 | 1.0 | 1.0 |
| Enantiomeric compound 8 | 1.20 | 1.27 | 1.12 | 1.21 | 1.26 |
| Enantiomeric compound 9 | 2.04 | 2.24 | 1.8 | 1.91 | 1.56 |
| Mean of α values | 1.56 | 1.68 | 1.43 | 1.47 | 1.45 |

TABLE 2

H/I = 90/10

| Filler | Ex. 1 | Ex. 2 | Ex. 3 | Ex. 4 |
|---|---|---|---|---|
| Silica gel | MA-Si | M-Si | MA-Si | MA-Si |
| Polysaccharide derivative | 6-CMDMPC | 6-CMDMPC | 6-CMDMPC | 6-CMDMPC |
| Third component | styrene | styrene | dimethyl-butadiene | dimethyl-butadiene |
| Addition amount (%) | 10 | 10 | 10 | 20 |
| Immobilization rate (%) | 90 | 80 | 91 | 93 |
| Enantiomeric compound 1 | 1.76 | 1.52 | 1.65 | 1.64 |
| Enantiomeric compound 2 | 1.27 | 1.45 | 1.23 | 1.25 |
| Enantiomeric compound 3 | 1.22 | 1.31 | 1.27 | 1.29 |
| Enantiomeric compound 4 | 1.11 | 1.12 | 1.15 | 1.14 |
| Enantiomeric compound 5 | 1.27 | 1.28 | 1.28 | 1.29 |
| Enantiomeric compound 6 | 1.91 | 2.35 | 2.13 | 2.14 |
| Enantiomeric compound 7 | 1.0 | 1.06 | 1.17 | 1.17 |
| Enantiomeric compound 8 | 1.15 | 1.20 | 1.17 | 1.18 |
| Enantiomeric compound 9 | 3.82 | 4.53 | 3.54 | 3.42 |

The enantiomeric compounds 1 to 9 in Tables 1 and 2 are as shown in the following Table 3.

TABLE 3

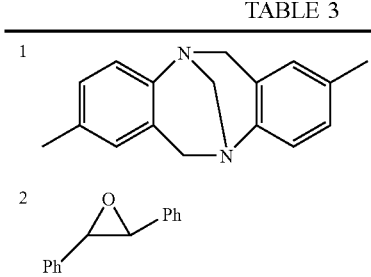

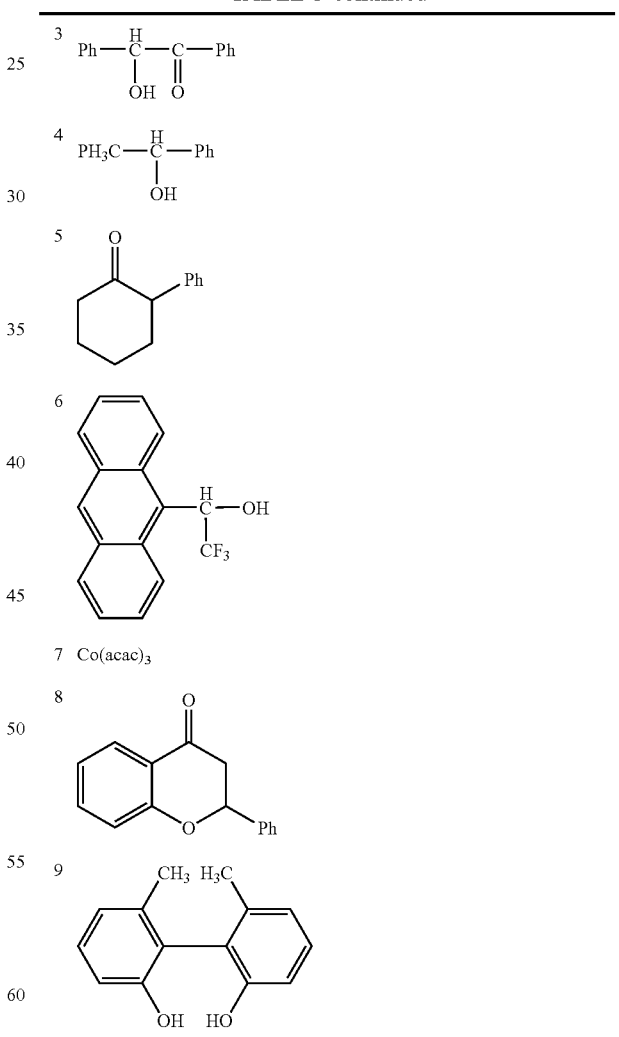

The means of the α values in Tables 1 and 2 are the means of the α values of nine enantiomeric compounds. An inseparate sample (ca. 1) was calculated as 1.0. It is generally said that the separation performance is reduced by about 10 to 20% in a chemically bond type filler compared to a supporting type filler currently used. However, the separation performance is sufficiently retained in Examples 1 and 2.

The invention claimed is:

1. A separating agent for enantiomeric isomers, comprising a polymerizable polysaccharide derivative having 5 to 35% of polymerizable unsaturated groups based on the hydroxyl groups of the polysaccharide, a polymerizable monomer having polymerizable unsaturated groups, said polymerizable monomer being styrene, and a carrier having polymerizable functional groups, the polymerizable polysaccharide derivative, the polymerizable monomer and the carrier having been copolymerized with one another to be chemically bound mutually such that the immobilization rate of the polysaccharide derivative is at least 80%.

2. The separating agent according to claim 1, wherein the polymerizable polysaccharide derivative is carried on the carrier having polymerizable functional groups and then is copolymerized with the polymerizable monomer.

3. The separating agent according to claim 1, wherein the polymerizable polysaccharide derivative has the polymerizable unsaturated groups at position 6.

4. The separating agent according to claim 1, comprising 1-50 parts by weight of the polymerizable monomer per 100 parts by weight of the polymerizable polysaccharide derivative.

5. The separating agent according to claim 1, wherein the polysaccharide making up the polymerizable polysaccharide derivative is amylose or cellulose.

6. The separating agent according to claim 5, wherein the polymerizable polysaccharide derivative is a cellulose phenylcarbamate derivative.

7. The separating agent according to claim 1, wherein the carrier having polymerizable functional groups is a silica gel having an acryl group or a methacryl group.

8. The separating agent according to claim 1, wherein the polymerizable monomer is styrene.

9. The separating agent according to claim 1, wherein the polymerizable polysaccharide derivative is a cellulose phenylcarbamate derivative, the polymerizable monomer is styrene and the carrier is a silica gel having an acryl group or a methacryl group.

10. The separating agent according to claim 1, wherein the immobilization rate of the polysaccharide derivative is at least 90%.

* * * * *